US011557226B2

(12) United States Patent
Mascart et al.

(10) Patent No.: US 11,557,226 B2
(45) Date of Patent: Jan. 17, 2023

(54) GASTROINTESTINAL TRACT SIMULATION SYSTEM, COMPARTMENTS THEREFOR, AND METHOD

(71) Applicant: PRODIGEST BVBA, Zwijnaarde (BE)

(72) Inventors: Louis-Philippe Mascart, Sint-Martens-Latem (BE); Massimo Marzorati, Brussels (BE); Tim Windels, Marke (BE); Sam Possemiers, Zwijnaarde (BE); Pieter Van Den Abbeele, Lokeren (BE)

(73) Assignee: PRODIGEST BVBA, Zwijnaarde (BE)

( * ) Notice: Subject to any disclaimer, the term of this patent is extended or adjusted under 35 U.S.C. 154(b) by 423 days.

(21) Appl. No.: 16/619,457

(22) PCT Filed: Jun. 6, 2018

(86) PCT No.: PCT/EP2018/064917
§ 371 (c)(1),
(2) Date: Dec. 4, 2019

(87) PCT Pub. No.: WO2018/224558
PCT Pub. Date: Dec. 13, 2018

(65) Prior Publication Data
US 2020/0168126 A1 May 28, 2020

(30) Foreign Application Priority Data
Jun. 6, 2017 (EP) .................................. 17174613

(51) Int. Cl.
*G09B 23/30* (2006.01)
*B01J 4/00* (2006.01)
(Continued)

(52) U.S. Cl.
CPC ............ *G09B 23/303* (2013.01); *B01J 4/001* (2013.01); *B01J 19/0066* (2013.01);
(Continued)

(58) Field of Classification Search
CPC ...... G09B 23/303; G09B 23/32; G09B 23/34; B01J 9/0073
(Continued)

(56) References Cited

U.S. PATENT DOCUMENTS 2,324,702 A * 7/1943 Hoffmann .............. G09B 23/32
264/222
3,595,530 A * 7/1971 Hubers ................... B01F 31/29
366/332
(Continued)

FOREIGN PATENT DOCUMENTS

CN 205740983 U 11/2016

OTHER PUBLICATIONS

International Search Report of PCT/EP2018/064917 dated Sep. 13, 2018.
(Continued)

*Primary Examiner* — Joseph B Baldori
(74) *Attorney, Agent, or Firm* — Polsinelli PC

(57) ABSTRACT

Gastrointestinal tract simulation system and compartment therefor. The compartment comprising a vessel having an open top surrounded by a peripheral edge portion and an air-tight lid system configured to be placed onto the peripheral edge portion. The lid system comprises a body with a plurality of passageways extending through the body and providing access to the interior of the vessel, the plurality of passageways comprising passageways for fluid transfer tubes and passageways for mounting at least one sensor component. The lid system is provided with releasable sealing elements for sealing the plurality of passageways and at least one pressing element which is common to at least a number of the sealing elements and configured for applying pressure to each of the respective sealing elements to effect the sealing of the respective passageways.

19 Claims, 10 Drawing Sheets

(51) Int. Cl.
  *B01J 19/00* (2006.01)
  *G09B 23/34* (2006.01)
  *G09B 23/32* (2006.01)

(52) U.S. Cl.
  CPC .......... *B01J 19/0073* (2013.01); *G09B 23/32* (2013.01); *G09B 23/34* (2013.01); *B01J 2219/085* (2013.01)

(58) Field of Classification Search
  USPC ........................................ 434/267, 268, 272
  See application file for complete search history.

(56) References Cited

U.S. PATENT DOCUMENTS

| | | | | |
|---|---|---|---|---|
| 4,457,339 | A | 7/1984 | Juan et al. | |
| 5,525,305 | A * | 6/1996 | Minekus | B01F 31/55 422/111 |
| 5,589,649 | A * | 12/1996 | Brinker | B01L 7/00 219/385 |
| 5,993,406 | A * | 11/1999 | Rozga | G09B 23/28 604/6.09 |
| 6,022,733 | A * | 2/2000 | Tam | C12M 29/16 435/298.2 |
| 6,379,619 | B1 * | 4/2002 | Rozga | G09B 23/28 604/4.01 |
| 6,488,507 | B1 * | 12/2002 | Stoloff | G09B 23/28 434/272 |
| 7,029,164 | B2 * | 4/2006 | Linsen | B01F 35/2132 366/261 |
| 7,144,727 | B2 * | 12/2006 | Akers | C12M 29/10 210/257.2 |
| 7,390,653 | B2 * | 6/2008 | Akers | C12M 23/06 210/321.89 |
| 8,092,222 | B2 * | 1/2012 | Wickham | B01F 33/821 434/127 |
| 8,257,085 | B2 * | 9/2012 | Alric | G09B 23/32 434/272 |
| 8,435,036 | B2 * | 5/2013 | Wickham | B01F 35/7547 434/127 |
| 9,314,404 | B2 * | 4/2016 | Gonzalez-Miranda | B01F 33/813 |
| 9,575,044 | B2 * | 2/2017 | Minekus | G09B 23/32 |
| 10,119,116 | B2 * | 11/2018 | Subhadra | C12M 23/06 |
| 10,127,839 | B2 * | 11/2018 | Legen | F04B 43/12 |
| 10,228,358 | B2 * | 3/2019 | Narang | G01N 33/15 |
| 10,287,539 | B2 * | 5/2019 | Tsumura | C12M 27/10 |
| 10,417,938 | B2 * | 9/2019 | Minekus | B01D 61/147 |
| 10,955,375 | B2 * | 3/2021 | Hoyt | G01N 27/48 |
| 2008/0206728 | A1 * | 8/2008 | Wickham | B01F 31/29 434/272 |
| 2011/0020780 | A1 * | 1/2011 | Alric | G09B 23/32 434/272 |
| 2018/0144662 | A1 * | 5/2018 | Tassone | G09B 23/306 |
| 2020/0168126 | A1 * | 5/2020 | Mascart | G09B 23/30 |

OTHER PUBLICATIONS

Written Opinion of PCT/EP2018/064917 dated Sep. 13, 2018.

Muetzel, S., "A Fermentation System for Rapid and Accurate Modelling of Rumen Function," Report for MAF, Farming, Food and Health First, pp. 2-13, Aug. 1, 2008.

Van den Abbeele, P., et al., "Microbial Community Development in a Dynamic Gut Model Is Reproducible, Colon Region Specific, and Selective for Bacteroidetes and Clostridium Cluster IX #" Applied and Environmental Microbiology, vol. 76, No. 15, pp. 5237-5246, Aug. 2010.

* cited by examiner

GASTROINTESTINAL TRACT SIMULATION SYSTEM, COMPARTMENTS THEREFOR, AND METHOD

CROSS-REFERENCE TO RELATED APPLICATIONS

This application is the 35 U.S.C. § 371 National Stage of International Application Number PCT/EP2018/064917, filed Jun. 6, 2018, which claims priority from European Application No. 17174613.4, filed on Jun. 6, 2017, the entire content of which is incorporated herein by reference.

FIELD OF THE INVENTION

The present invention relates to a gastrointestinal tract simulation system, a compartment for such a system, and a method of operating such a system. The gastrointestinal tract simulation system can be a simulator for any monogastric animal (including humans).

BACKGROUND ART

The conventional SHIME is a dynamic model of the human gut comprising 5 compartments respectively simulating the stomach, small intestine and ascending, transverse and descending colon. The stomach and small intestine compartments mimic the enzymatic and physicochemical environment by controlling pH and residence time and the dosing of a proper nutritional medium, enzymes and bile salts.

By controlling the pH, redox potential and residence times, the different colon compartments each harbor a microbial community that corresponds to that of the in vivo situation in terms of metabolic activity and community composition. In this model a typical stabilization period of two weeks and a basal period of two weeks are followed by treatment and wash-out periods.

In order to simulate the operation of the gastrointestinal tract, various fluids need to be added to the compartments. Furthermore, tubes are needed to transfer the contents from one compartment to another, and openings are needed for mounting sensors. As a result, the air-tight sealing of the compartments is cumbersome.

From U.S. Pat. No. 4,457,339, a pinch valve module is known which can be used in a.o. in an automated analysis apparatus for performing tests in the medical and biological fields.

SUMMARY OF THE INVENTION

It is an aim of the present invention to provide a compartment of a gastrointestinal tract simulation system with which the air-tight sealing can be facilitated.

It is another aim of the present invention to provide an improved fluid transfer system for transferring fluids into and from compartments of a gastrointestinal tract simulation system.

It is another aim of the present invention to provide an improved stirring system for stirring the contents of compartments of a gastrointestinal tract simulation system.

It is another aim of the present invention to provide a method of simulating the functioning of the human or animal gastrointestinal tract.

A first aspect of the invention provides a compartment of a gastrointestinal tract simulation system, comprising a vessel having an open top surrounded by a peripheral edge portion and an air-tight lid system configured to be placed onto the peripheral edge portion and to form an air-tight seal between the lid system and the vessel, wherein the lid system comprises a body with a plurality of passageways extending through the body and providing access to the interior of the vessel, said plurality of passageways comprising first passageways configured for receiving fluid transfer tubes and second passageways configured for mounting at least one sensor component, and wherein the lid system is provided with releasable sealing elements for sealing the plurality of passageways and at least one pressing element which is common to at least a number of the sealing elements and configured for applying pressure to each of the respective sealing elements to effect the sealing of the respective passageways.

By the provision of the releasable sealing elements in combination with the common pressing element, the air-tight sealing of the compartment may be facilitated and/or simplified. One only needs to operate the pressing element to effect, or release, the sealing of the passageways by the sealing elements. A further advantage of this structure is that it makes it possible to miniaturize the compartments of the gastrointestinal tract simulation system.

In embodiments according to the invention, the releasable sealing elements may each comprise a sealing member in a sealing material, provided for being compressed onto or around the respective tube or sensor component which is inserted in the respective passageway, and a spring member, for example a helical spring, acting on the sealing member for said compression. This provides a simple construction for the sealing elements. This embodiment may provide a simple construction for the releasable sealing elements.

In embodiments according to the invention, the pressing element may comprise a plate-like member which is movably fixed to the body of the lid system between a pressing position, in which the plate-like member applies the pressure to the sealing elements to effect the sealing of the passageways, and a release position, in which the sealing elements are in released state. The movable fixture may for example be carried out by means of one or more screws, wherein the plate-like member is movable from the release position to the pressing position by screwing in the one or more screws, and vice versa. This embodiment may provide a simple construction for the pressing member.

In embodiments according to the invention, the body of the air-tight lid system may be hollow with an internal cavity, the releasable sealing elements being arranged in the hollow body surrounding said cavity, and a holding element may be provided in said cavity, said holding element containing said first and second passageways for said tubes and said sensor components. This embodiment has the advantage that the lid system is easily adaptable to circumstances, like the number and size of tubes and sensor components that need to be provided through the lid system. In this way, it can be sufficient to provide a different holding element for each different compartment of the gastrointestinal tract simulation system, avoiding the need to design a complete lid system for each compartment. Furthermore, this holding element can be separately designed from the outer parts of the lid system and hence optimized to guide the tubes from the point of entry into the lid system to the point of exit and into the interior of the vessel, e.g. with passageways having gentle curves for the tubes. A further advantage of this structure is that it makes it possible to miniaturize the compartments of the gastrointestinal tract simulation system. The holding element may for example be a 3D printed part.

In embodiments according to the invention, the pressing element or plate-like member may comprise cut-outs, i.e. have a shape with cut-outs, for example leaving space for fixing screws, by means of which the body of the lid system and the vessel are sealed to each other.

In embodiments according to the invention, the compartment may comprise a sensor probe extending vertically through the lid system into the vessel, "vertically" meaning in a direction parallel to a height axis of the vessel. The passageways may likewise extend vertically through the lid system. Further, the passageways may be radially spaced around the sensor probe. This configuration may reduce the overall space occupied by, or needed for, the probe and passageways, resulting in a compact lid system.

The construction with holes for the sensor probe, passageways, and/or screws for fixing the plate-like member onto the body and/or sealing the body onto the vessel, preferably all extending parallel to each other, preferably vertically, has the advantage that manufacturing of the body of the lid system may be facilitated or simplified, reducing manufacturing complexity and/or costs. The body may for example be manufactured from a body of plastic material, with the various holes being drilled into the body from the same direction.

In embodiments according to the invention, the body and the pressing element or plate-like member may be rotationally symmetric parts. This can further reduce manufacturing complexity.

A second aspect of the invention, which may occur in combination with the other aspects and embodiments of the invention described herein, provides a gastrointestinal tract simulation system comprising at least one compartment, each compartment comprising a vessel having an open top surrounded by a peripheral edge portion and an air-tight lid system configured to be placed onto the peripheral edge portion and to form an air-tight seal between the lid system and the vessel, wherein the lid system comprises a body with a plurality of passageways extending through the body and providing access to the interior of the vessel, said plurality of passageways comprising first passageways configured for receiving fluid transfer tubes and second passageways configured for mounting at least one sensor component, fluid transfer tubes extending through the respective first passageways and sensor components mounted in or on the second passageways. The gastrointestinal tract simulation system further comprises a fluid transfer system for transferring fluids into and from said compartments, said fluid transfer system comprising a plurality of pumps, preferably syringe pumps, for pumping fluid via said fluid transfer tubes into and from said compartments, and a pinch valve system with pinch valves, each pinch valve being configured for opening and closing one of said liquid transfer tubes, wherein the pinch valve system comprises a plurality of cam discs, one for each pinch valve, and a common spindle for synchronously driving the rotation of the cam discs.

By the provision of the individual cam discs for each pinch valve in combination with the common drive spindle, the setting or "programming" of the operation sequence of the pinch valves may be simplified: one simple needs to provide a cam disc with an appropriate shape for each pinch valve, e.g. with protrusions or cams as desired to control the opening and closing of the pinch valve as desired. The common drive spindle, for example driven by means of a stepper motor, can assure synchronised rotation of the individual cam discs. To alter the operation of one pinch valve, one simple has to take out the respective cam disc and replace it with another cam disc.

In embodiments according to the invention, the cam discs may be assembled on the common spindle, wherein the common spindle has a rotation locking shape with the cam discs having a central opening corresponding to said rotation locking shape. This may simplify the construction of the pinch valve system. (In other embodiments, the rotation of the cam discs may also be driven by means of a gear system and/or the cam discs may be rotationally locked to each other in other ways.)

In embodiments according to the invention, the pinch valves may comprise spring-loaded fingers which are actuated by cams on the cam discs. In other embodiments, the pinch valves may be formed by cams on the cam discs themselves.

A third aspect of the invention, which may occur in combination with the other aspects and embodiments of the invention described herein, provides a gastrointestinal tract simulation system comprising at least one compartment, each compartment comprising a vessel having an open top surrounded by a peripheral edge portion and an air-tight lid system configured to be placed onto the peripheral edge portion and to form an air-tight seal between the lid system and the vessel, wherein the gastrointestinal tract simulation system further comprises a water bath in which the at least one vessel of the at least one compartment is placed and at least one magnetic stirring system for stirring the contents of at least one vessel, the magnetic stirring system comprising a magnetic drive mounted underneath the respective vessel and the water bath and provided for generating a rotating magnetic field, a permanent magnet located in the water bath underneath the respective vessel and provided for rotating with and amplifying said rotating magnetic field, and a first stirring element at the bottom of the respective vessel provided for being rotated by said amplified magnetic field.

By the provision of this magnetically driven stirring element, the need for a mechanical coupling of the stirring element through the wall of the vessel or the lid can be avoided, and as a result the air-tight sealing of the interior of the compartment can be better assured. The provision of the permanent magnet in the water bath which rotates along and amplifies the generated magnetic field can ensure a good operation of the stirring element in the vessel. Furthermore, the rotation of the permanent magnet in the water bath also stirs the contents of this water bath and can lead to a more homogeneous temperature.

In preferred embodiments, the vessel of the respective compartment may be an outer vessel and the compartment may further comprise an inner vessel mounted inside the outer vessel and a second stirring element at the bottom of the inner vessel, provided for being rotated by the amplified magnetic field as well.

In preferred embodiments, the first and/or second stirring element may also be a permanent magnet.

In preferred embodiments, the permanent magnet in the water bath, the first stirring element and/or the second stirring element may be generally triangular prism-shaped.

A fourth aspect of the invention, which may occur in combination with the other aspects and embodiments of the invention described herein, provides a gastrointestinal tract simulation system comprising at least one compartment which has an outer vessel having an open top surrounded by a peripheral edge portion and an air-tight lid system configured to be placed onto the peripheral edge portion and to form an air-tight seal between the lid system and the vessel, wherein the gastrointestinal tract simulation system further comprises an inner vessel mounted inside the outer vessel, the inner vessel having a wall at least part of which is formed by a dialysis membrane. In this way, the inner vessel can be used to mimic the adsorption of small digested compounds in the intestines, with the membrane mimicking the blood-intestine barrier.

In preferred embodiments, the inner vessel wall comprises a cylindrical grid structure surrounded by said dialysis membrane.

A fifth aspect of the invention, which may occur in combination with the other aspects and embodiments of the invention described herein, provides a gastrointestinal tract simulation system comprising at least one compartment which contains carriers covered with mucin representative of the mucus layer lining the gut wall to simulate a mucosal compartment that can support the colonization of microbial species which may grow attached to the gut wall in humans and animals.

A sixth aspect of the invention, which may occur in combination with the other aspects and embodiments of the invention described herein, provides a compartment for a gastrointestinal tract simulation system comprising a vessel having an open top surrounded by a peripheral edge portion and an air-tight lid system configured to be placed onto the peripheral edge portion and to form an air-tight seal between the lid system and the vessel, the lid system being provided with a high liquid level detection means for detecting a too high liquid level in the vessel, the high liquid level detection means comprising a gas inlet tube and a gas outlet tube through the lid system and a means for establishing a gas flow through said gas inlet and outlet tubes, wherein a floater is mounted at a mouth of at least one of the gas inlet and outlet tubes, said floater being adapted for raised, by floating on liquid in the vessel if the level of said liquid becomes too high, from a free flow position in which the floater forms no obstruction for said gas flow to an obstructing position in which the floater forms an obstruction for said gas flow.

A seventh aspect of the invention, which may occur in combination with the other aspects and embodiments of the invention described herein, provides a method of simulating the functioning of the human or animal gastrointestinal tract, comprising the steps of filling empty compartments of a gastrointestinal tract simulation system as defined herein with fluids simulating the physiological fluids of the gastrointestinal tract and operating the gastrointestinal tract simulation system so as to control, in each of the compartments, one or more or all of the following parameters: liquid flow, temperature, pH, ionic strength, head space, stirring, pressure, liquid volume, each in accordance with pre-determined values, ranges or trajectories.

By using the gastrointestinal tract simulating system according to embodiments described herein, one can test 10-fold smaller quantities of test product compared to the conventional SHIME apparatus. Further, the present invention overcomes the limited throughput of the conventional SHIME apparatus, i.e. 2 complete intestines or 4 limited setups, and allows for example to study 6 complete intestines, 12 limited setups in 3-step configuration or the possibility to run 30 individual reactors.

BRIEF DESCRIPTION OF THE DRAWINGS

The present invention will be discussed in more detail below, with reference to the attached drawings, in which.

DESCRIPTION OF EMBODIMENTS

Figure 1:
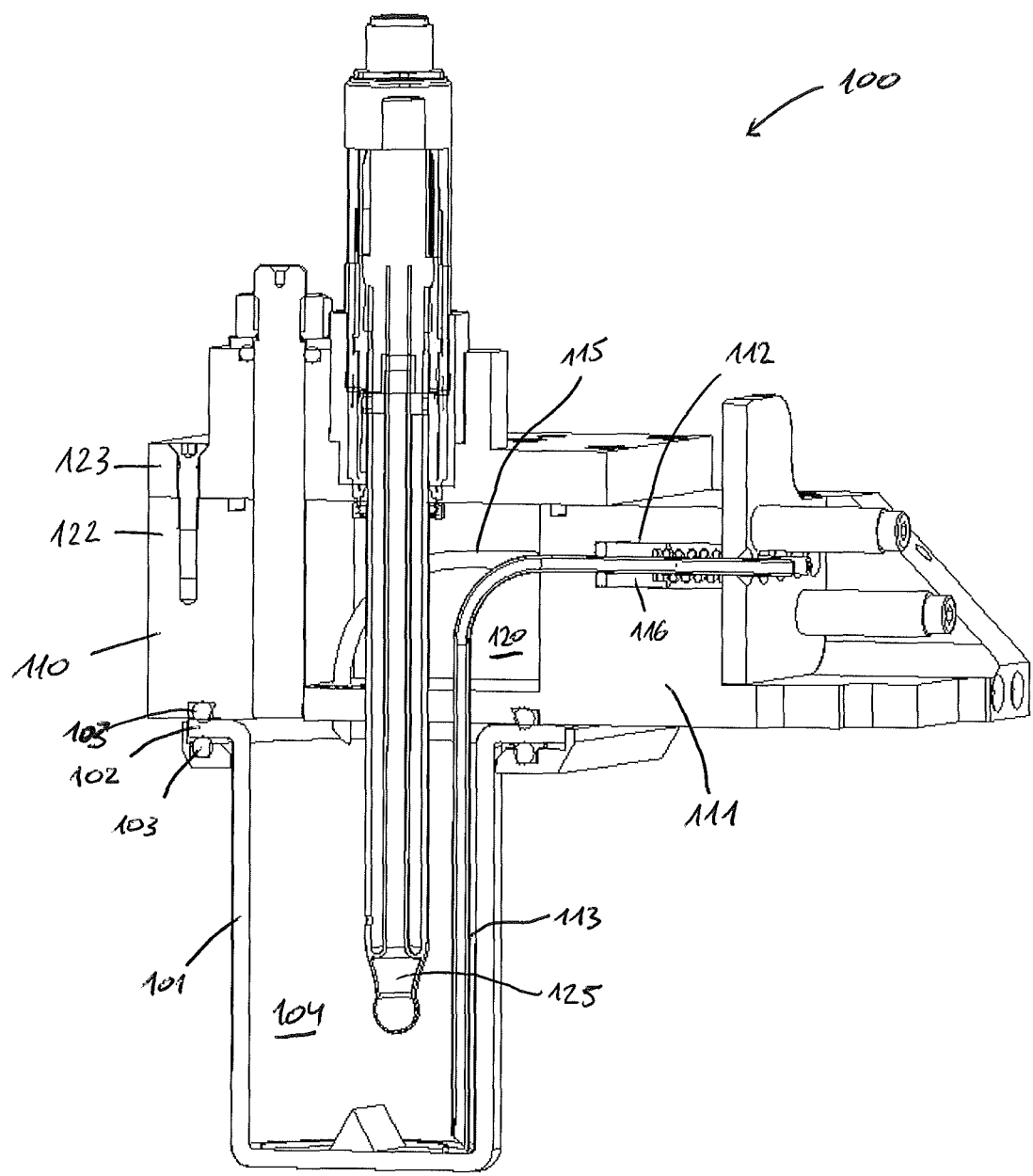
FIG. 1 shows a cross-sectional view of a compartment for a gastrointestinal tract simulating system according to an embodiment of the invention.

The present invention will be described with respect to particular embodiments and with reference to certain drawings but the invention is not limited thereto but only by the claims. The drawings described are only schematic and are non-limiting. In the drawings, the size of some of the elements may be exaggerated and not drawn on scale for illustrative purposes. The dimensions and the relative dimensions do not necessarily correspond to actual reductions to practice of the invention.

Furthermore, the terms first, second, third and the like in the description and in the claims, are used for distinguishing between similar elements and not necessarily for describing a sequential or chronological order. The terms are interchangeable under appropriate circumstances and the embodiments of the invention can operate in other sequences than described or illustrated herein.

Moreover, the terms top, bottom, over, under and the like in the description and the claims are used for descriptive purposes and not necessarily for describing relative positions. The terms so used are interchangeable under appropriate circumstances and the embodiments of the invention described herein can operate in other orientations than described or illustrated herein.

Furthermore, the various embodiments, although referred to as "preferred" are to be construed as exemplary manners in which the invention may be implemented rather than as limiting the scope of the invention.

The term "comprising", used in the claims, should not be interpreted as being restricted to the elements or steps listed thereafter; it does not exclude other elements or steps. It needs to be interpreted as specifying the presence of the stated features, integers, steps or components as referred to, but does not preclude the presence or addition of one or more other features, integers, steps or components, or groups thereof. Thus, the scope of the expression "a device comprising A and B" should not be limited to devices consisting only of components A and B, rather with respect to the present invention, the only enumerated components of the device are A and B, and further the claim should be interpreted as including equivalents of those components.

Figure 2:
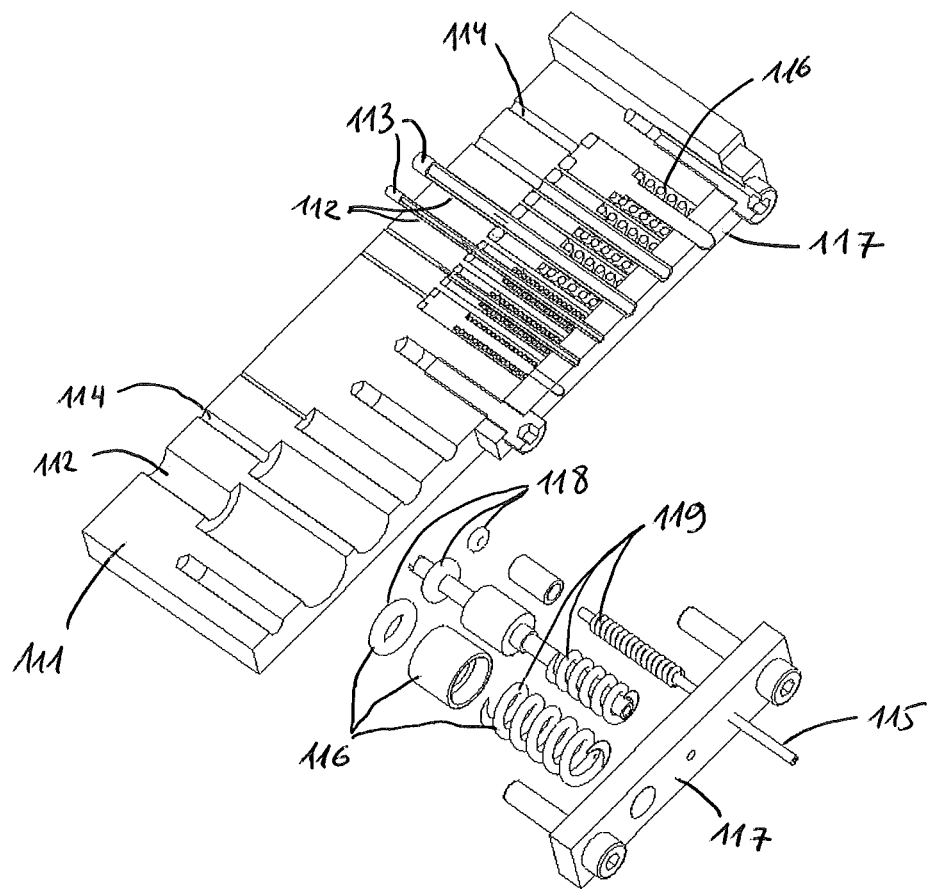
FIG. 2 shows in exploded view a cross-section through a part of the compartment of FIG. 1, comprising releasable sealing elements.

An embodiment, as shown in FIGS. 1-2, provides a compartment 100 (also called reactor) of a gastrointestinal tract simulation system, comprising a vessel 101 having an open top surrounded by a peripheral edge portion 102 and an air-tight lid system 110 configured to be placed onto the peripheral edge portion and to form an air-tight seal between the lid system and the vessel. This means that the lid system 110 is configured to fit on the peripheral edge portion 102 in such a way that, following a step of fixing the lid system on said edge portion, an air-tight seal is obtained. This can be achieved in many ways, for example involving one or more sealing rings 103, which are known per se to the person skilled in the art, and therefore need not be further described herein.

The lid system comprises a body 111 with a plurality of passageways 112, 113 extending through the body and providing access to the interior 104 of the vessel, said plurality of passageways comprising first passageways 112 configured for receiving fluid transfer tubes 113 and second passageways 114 configured for mounting at least one sensor component 115 (which may also comprise tubing). This means that the first passageways are sized and formed for receiving fluid transfer tubes (for transferring liquids and/or gases), in such a way that they preferably fit tightly around the tubes and guide them between the point of entry into the lid system and the point of exit towards the interior of the vessel, preferably so as to obtain gentle corners to avoid obstructions, and that the second passageways are configured for accommodating a sensor or at least a component of a sensor, which is in turn provided for sensing a parameter in the interior of the vessel.

The lid system 110 is preferably provided with releasable sealing elements 116 for sealing at least the first passageways and one or more pressing elements 117 which is/are common to at least a number of the sealing elements and configured for applying pressure to each of the sealing elements to effect the sealing of the plurality of passageways. In the embodiment shown in FIG. 2, the sealing elements 116 each comprise a helical spring, a cylindrical member and a resilient sealing ring, which in use surround the tubing with the sealing ring being compressed onto and around the tubing. By this construction, the air-tight sealing of the compartment may be facilitated and/or simplified. One only needs to operate the pressing element 117 to effect, or release, the sealing of all of the number of passageways by the sealing elements 116, or at least those passageways which have a sealing element operated by the common pressing element 117. A further advantage of this structure is that it makes it possible to miniaturize the compartments of the gastrointestinal tract simulation system.

In embodiments, the releasable sealing elements 116 may each comprise a sealing member 118 in a sealing material, provided for being compressed onto or around the respective tube or sensor component which is inserted in the respective passageway, and a spring member 119, for example a helical spring, acting on the sealing member to effectuate said compression. This provides a simple construction for the sealing elements.

In embodiments, the pressing element may comprise a plate-like member 117 which is movably fixed to the body of the lid system between a pressing position, in which the plate-like member applies the pressure to the sealing elements to effect the sealing of the passageways, and a release position, in which the sealing elements are in released state. The movable fixture may for example be carried out by means of one or more screws, wherein the plate-like member is movable from the release position to the pressing position by screwing in the one or more screws, and vice versa. This embodiment may provide a simple construction for the pressing member.

In embodiments, the body 111 of the air-tight lid system may be hollow with an internal cavity 120, the releasable sealing elements being arranged in the hollow body surrounding said cavity, and a holding element (not shown) may be provided in said cavity, said holding element containing part of said first and second passageways for said tubes and said sensor components. In this embodiment, the body of the lid system may be carried out in two parts, namely a bottom part 122 which is provided for being fixed on the vessel and a top part 123, with the cavity between the two. In this embodiment, the releasable sealing elements 116 may be arranged on, preferably integrated in the walls of the bottom part and/or the top part of the hollow body, which surround the cavity, and the internal cavity may contain a holding element which defines the desired shape of all of the passageways, in particular from the position of the respective sealing element up to the interior of the vessel. The top part 123 of the body is arranged to close off the internal cavity 120, to which end the top and bottom parts may be provided with mating screw-threads and a sealing ring to seal off the cavity. This embodiment has the advantage that the lid system is easily adaptable to circumstances, like the number and size of tubes 113 and sensor components 115 that need to be provided through the lid system. In this way, it can be sufficient to provide a different holding element 121 for each different compartment of the gastrointestinal tract simulation system, avoiding the need to design a complete lid system for each compartment. In other words, the lid system of each of the compartments may be the same except for the holding element. Furthermore, this holding element 121 can be separately designed from the outer parts of the lid system and hence optimized to guide the tubes from the point of entry into the lid system to the point of exit and into the interior of the vessel, e.g. with passageways having gentle curves for the tubes A further advantage of this structure is that it makes it possible to miniaturize the compartments of the gastrointestinal tract simulation system.

The holding element (not shown) may for example be a 3D printed part, for example in polyamide or another material suitable for 3D printing. The body 111 of the lid system, in particular the top and bottom parts, may for example be manufactured in a plastic material, for example also a material suitable for 3D printing. The vessel 101 is preferably manufactured in a transparent material to enable visual inspection of the contents of the compartment.

The compartment 100 may be equipped with a pH probe 125, as shown, which may be centrally located and provided through the holding element which is provided in the cavity 120. So the holding element may provide all the passageways for all the tubing around a central opening for the pH probe, and thereby directing all the tubing to the right location in the vessel 101.

In embodiments, as a result of the structure described above, the compartments of the gastrointestinal tract simulation system may be miniaturized such that the vessel has, for example, an inner volume ranging from 5 ml to 100 ml.

Figure 3:
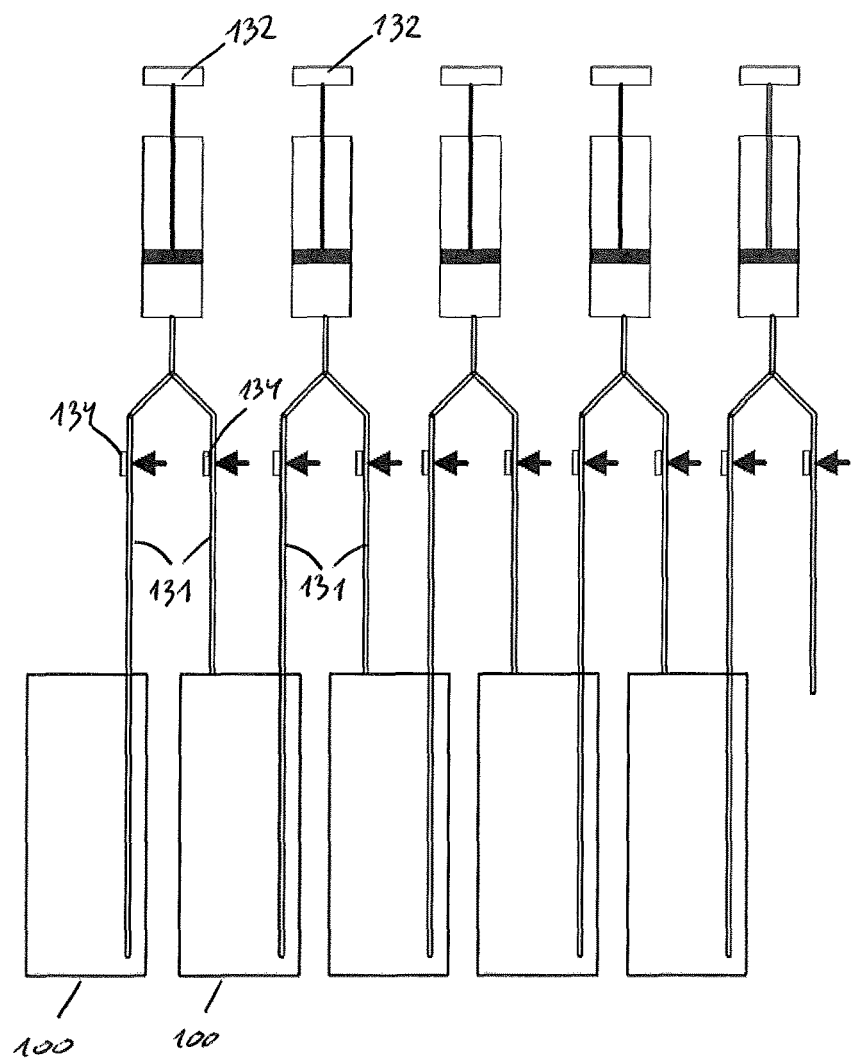
FIG. 3 shows a schematic view of a fluid transfer system for a gastrointestinal tract simulating system according to an embodiment of the invention.
Figure 4:
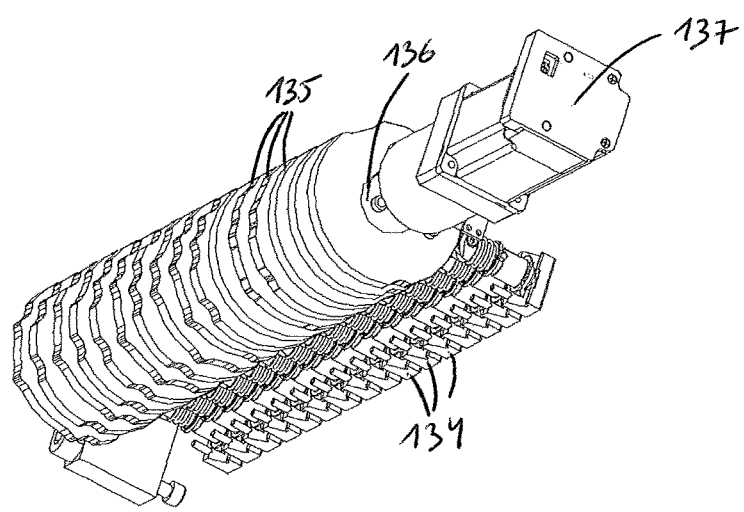
FIG. 4 shows a perspective view of a pinch valve system for the fluid transfer system of FIG. 3.
Figure 5:
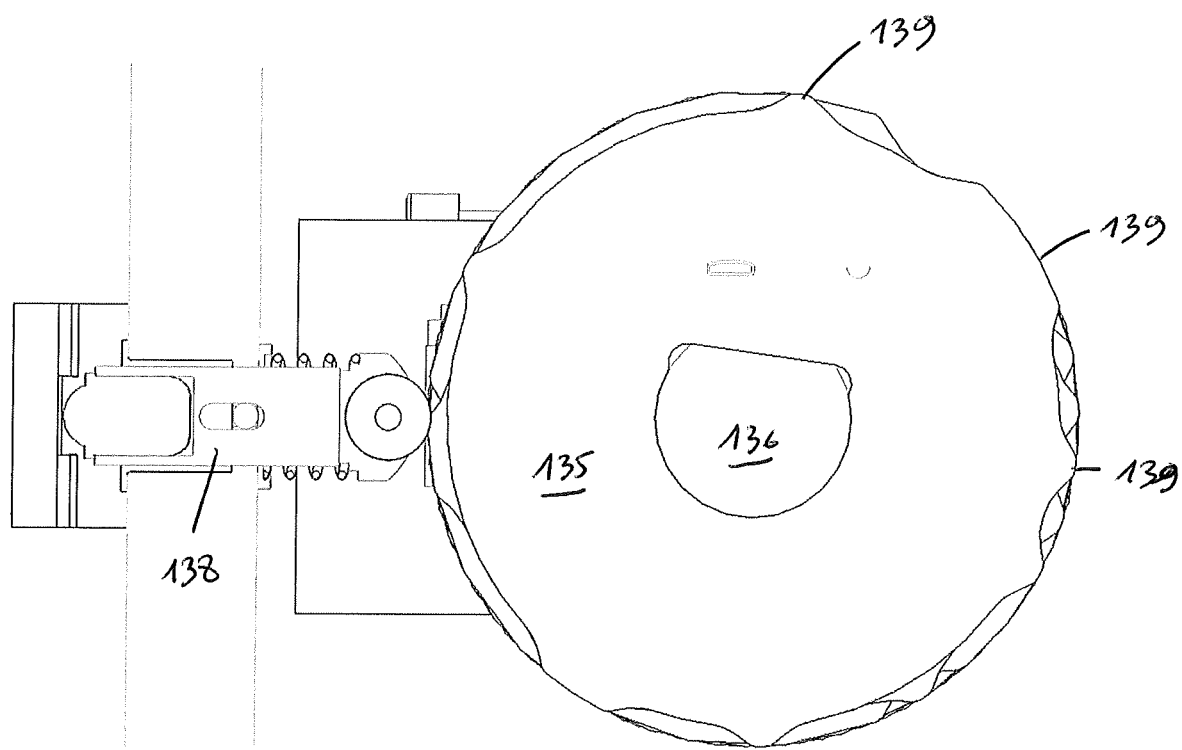
FIG. 5 shows a detail of the pinch valve system of FIG. 4.

An embodiment, as shown in FIGS. 3-5, provides a gastrointestinal tract simulation system comprising at least one compartment 100, for example as described above. The gastrointestinal tract simulation system further comprises a fluid transfer system for transferring fluids into and from said compartments.

The fluid transfer system preferably comprises a plurality of pumps, preferably syringe pumps 132, for pumping fluid via fluid transfer tubes 131 into and from said compartments 100, and a pinch valve system 133 with pinch valves 134, each pinch valve being configured for opening and closing one of said fluid transfer tubes 131, wherein the pinch valve system comprises a plurality of cam discs 135, one for each pinch valve, and a common spindle 136 for synchronously driving the rotation of the cam discs. By this construction, the setting or "programming" of the operation sequence of the pinch valves may be simplified: one simple needs to provide a cam disc with an appropriate shape for each pinch valve, e.g. with protrusions or cams as desired to control the opening and closing of the pinch valve as desired. The common drive spindle, for example driven by means of a stepper motor 137, can assure synchronised rotation of the individual cam discs. To alter the operation of one pinch valve, one simple has to take out the respective cam disc and replace it with another cam disc.

In embodiments according to the invention, the cam discs may be assembled on the common spindle, wherein the common spindle has a rotation locking shape with the cam discs having a central opening corresponding to said rotation locking shape. This may simplify the construction of the pinch valve system.

In other embodiments, the rotation of the cam discs may also be driven by means of a gear system and/or the cam discs may be rotationally locked to each other in other ways.

In embodiments, the pinch valves may comprise spring-loaded fingers 138 which are actuated by cams 139 on the cam discs. The cam discs may be configured for moving the fingers 138 between 3 positions: a fully closed position in which the finger 138 closes the tube 131, an 80% open position in which the tube is open but still clamped by the finger 138, and a fully open position in which the finger 138 releases the tube so that it can be removed from the pinch valve system and replaced.

In other embodiments, the pinch valves may be formed by cams on the cam discs themselves.

In embodiments, there may be a number of serially arranged compartments in the gastrointestinal tract simulation system, for example 2 to 10 serially arranged compartments, typically 5 serially arranged compartments.

Figure 6:
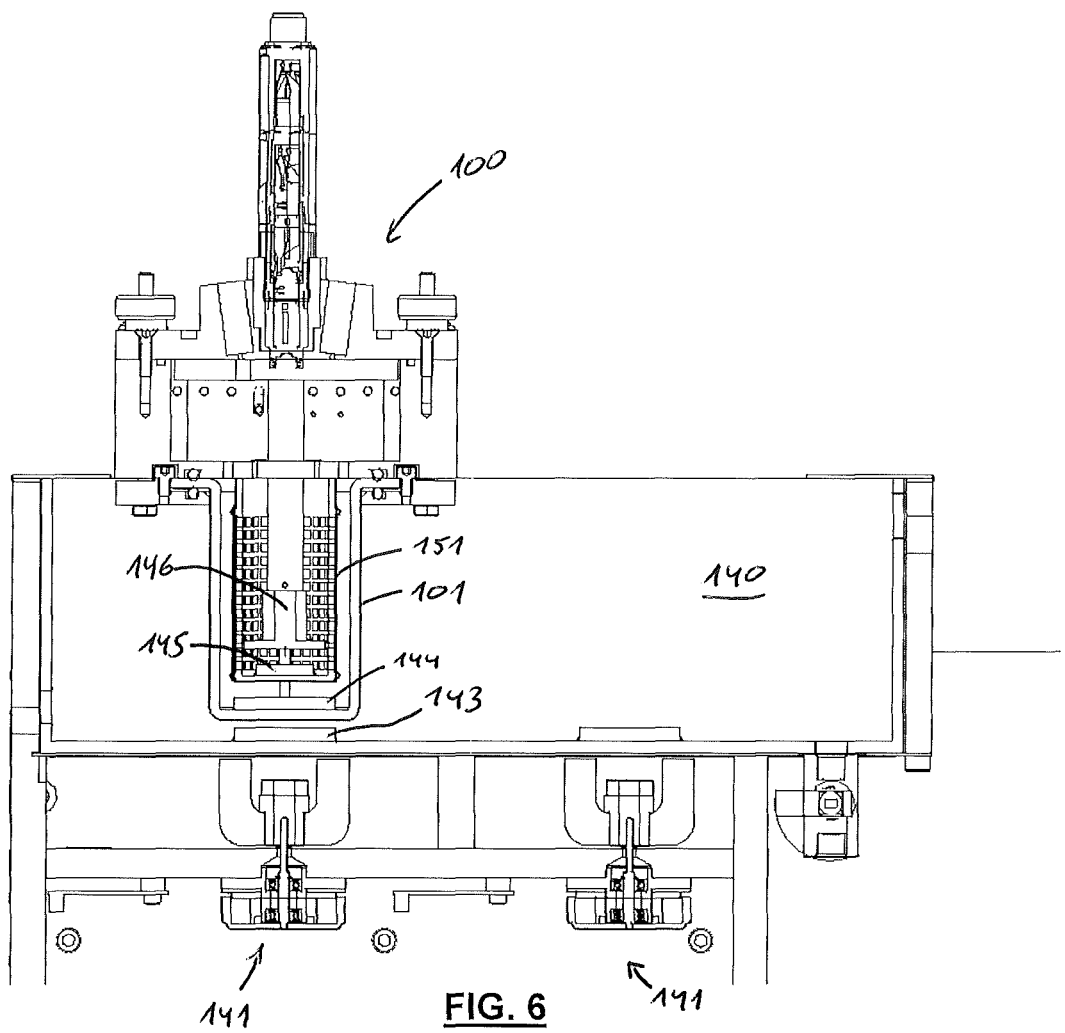
FIG. 6 shows a cross-sectional view of a gastrointestinal tract simulating system according to an embodiment of the invention, comprising a magnetic stirring system.
Figure 7:
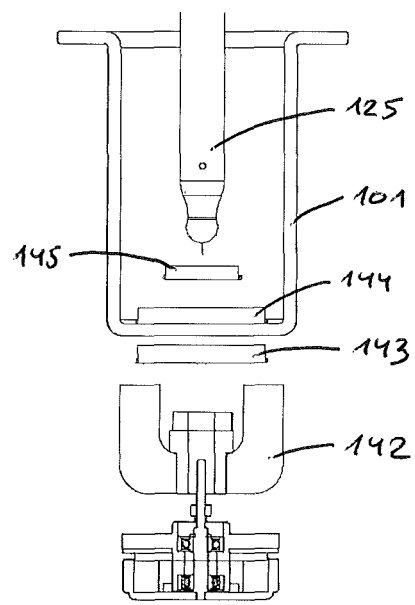
FIG. 7 shows a detail of the magnetic stirring system of FIG. 6.

In embodiments, as shown in FIGS. 5-6, a gastrointestinal tract simulation system is provided, comprising at least one compartment 100, for example as described above, wherein the gastrointestinal tract simulation system further comprises a water bath 140 in which the at least one vessel of the at least one compartment is placed and at least one magnetic stirring system 141 for stirring the contents of at least one vessel, the magnetic stirring system comprising a magnetic drive 142, for example a rotating electromagnet, mounted underneath the respective vessel 101 and the water bath 140 and provided for generating a rotating magnetic field, a permanent magnet 143 located in the water bath underneath the respective vessel and provided for rotating with and amplifying said rotating magnetic field, and a first stirring element 144 at the bottom of the respective vessel 101 provided for being rotated by said amplified magnetic field.

By the provision of this magnetically driven stirring element, the need for a mechanical coupling of the stirring element through the wall of the vessel or the lid can be avoided, and as a result the air-tight sealing of the interior of the compartment can be better assured. The provision of the permanent magnet 143 in the water bath which rotates along and amplifies the generated magnetic field can ensure a good operation of the stirring element in the vessel. Furthermore, the rotation of the permanent magnet 143 in the water bath also stirs the contents of this water bath and can lead to a more homogeneous temperature.

In preferred embodiments, the vessel of the respective compartment may be an outer vessel and the compartment may further comprise an inner vessel 151 mounted inside the outer vessel and a second stirring element 145 at the bottom of the inner vessel, provided for being rotated by the amplified magnetic field as well. An example of such an embodiment is shown in FIG. 8 and will be described further below.

In preferred embodiments, the first and/or second stirring element 144, 145 may also be a permanent magnet.

In preferred embodiments, the permanent magnet 143 in the water bath, the first stirring element 144 and/or the second stirring element 145 may be generally triangular prism-shaped. They may be freely moving elements in the respective water bath/vessel, or be held in position by means of an additional positioning element (not shown). In the embodiment shown in FIG. 5, further a probe support element 146 is provided at the bottom of the vessel 101 to support the pH sensor probe 125 and avoid contact between the probe and the stirring element 144.

Figure 8:
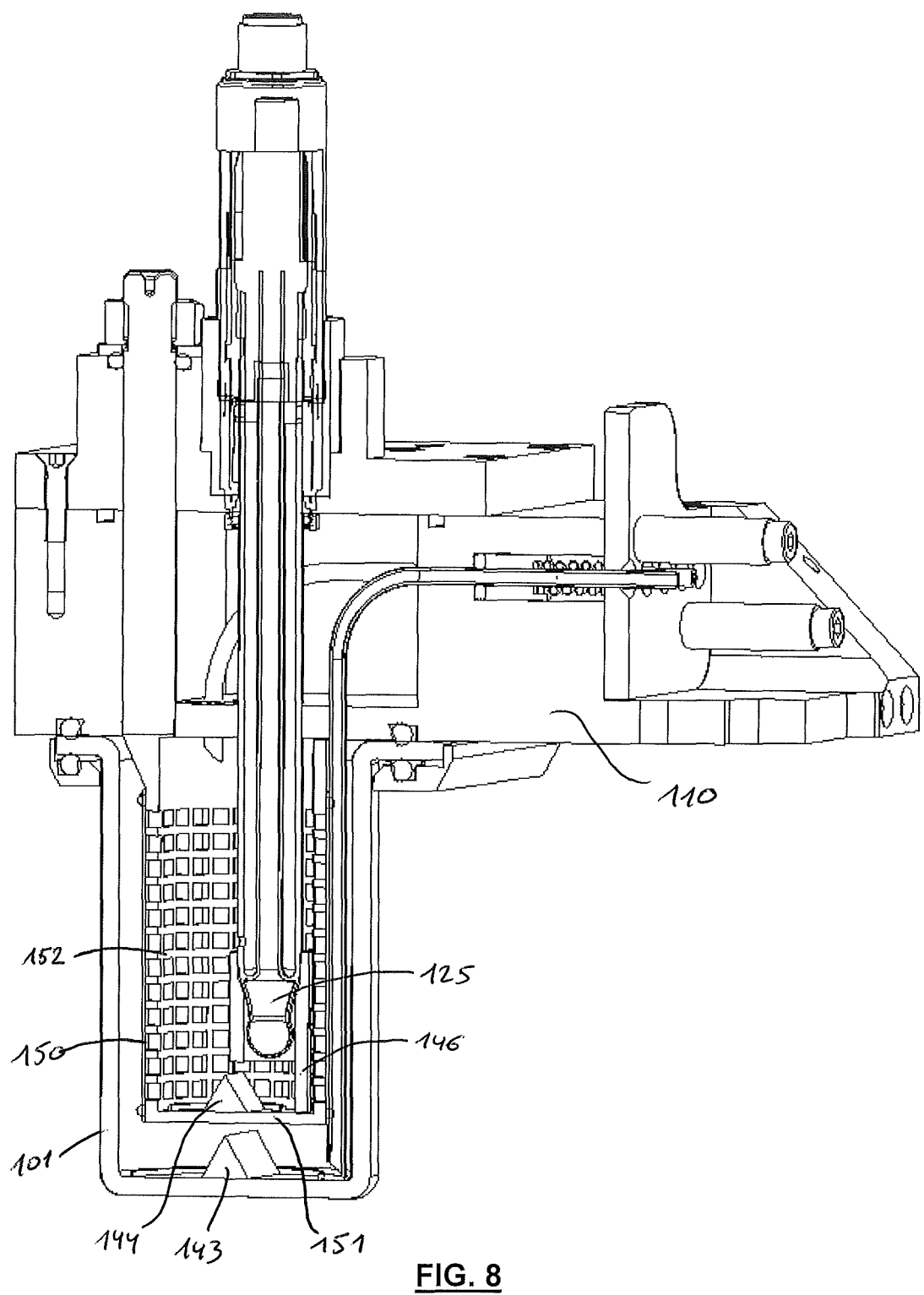
FIG. 8 shows a cross-sectional view of a compartment for a gastrointestinal tract simulating system according to another embodiment of the invention, comprising an inner vessel and an outer vessel.

In embodiments, as shown in FIG. 8, a gastrointestinal tract simulation system is provided, comprising at least one compartment which has an outer vessel 101 having an open top surrounded by a peripheral edge portion 102 and an air-tight lid system 110 configured to be placed onto the peripheral edge portion and to form an air-tight seal between the lid system and the vessel, and an inner vessel 151 mounted inside the outer vessel, the inner vessel having a wall at least part of which is formed by a dialysis membrane 150. In this way, the inner vessel can be used to mimic the adsorption of compounds in the intestines, with the membrane mimicking the blood-intestine barrier.

In preferred embodiments, the inner vessel wall comprises a cylindrical grid structure 152 surrounded by said dialysis membrane.

Figure 9:
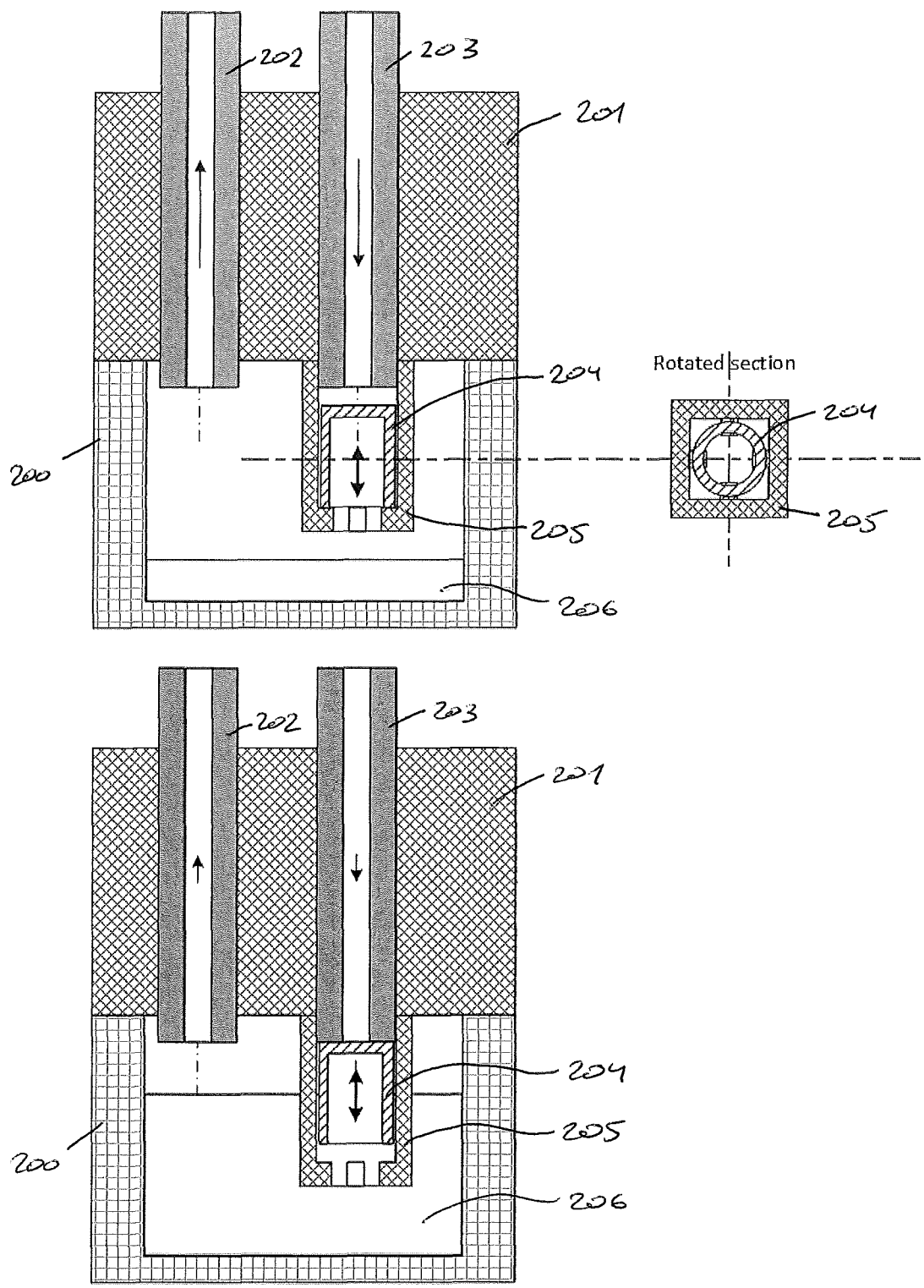
FIG. 9 shows schematic views of a high liquid level detection system for a compartment of a gastrointestinal tract simulating system according to an embodiment of the invention.

In a reactor vessel, it is preferred that the gas input and output tubing stays out of reach of the vessel liquid. A high liquid level detection is used to generate an emergency stop when liquid is supplied to the vessel and could reach the gas tubes. In small reactors (e.g. 25 mm diameter) like the ones described herein and wording under a pressure different from the atmospheric pressure and being able to be sterilized, prior art solutions for high liquid level detection are not suitable or bulky and expensive. Thereto, an embodiment according to the invention, shown in FIG. 9 provides a compartment for a gastrointestinal tract simulation system comprising a vessel 200 having an open top surrounded by a peripheral edge portion and an air-tight lid system 201 configured to be placed onto the peripheral edge portion and to form an air-tight seal between the lid system and the vessel, the lid system being provided with a high liquid level detection means 202-205 for detecting a too high liquid level in the vessel, the high liquid level detection means comprising a gas inlet tube 203 and a gas outlet tube 202 through the lid system 201 and a means (not shown, for example a small pump or ventilator or the like) for establishing a gas flow through said gas inlet and outlet tubes. A floater 204 is mounted at a mouth of the inlet tube 203 (could also be at the mouth of the outlet tube or both) and is adapted for raised, by floating on liquid 206 in the vessel if the level of said liquid becomes too high, from a free flow position (shown in FIG. 9 top) in which the floater forms no obstruction for said gas flow to an obstructing position (shown in FIG. 9 bottom) in which the floater forms an obstruction for said gas flow.

In the embodiment shown, the floater 204 takes the form of a hollow cylinder placed in a holder 205 with a square cross-section, so that gas flow can take place around the cylinder. It is evident that this can be carried out in many ways. Normally, under the influence of gravity, the floater 204 is located in downward position at a small distance from the mouth of the tube 203, so that free flow of the gas is possible. When the liquid level becomes too high, the floater 204 is moved upwards until its upper face reaches the mouth of the inlet tube 203 and obstructs the gas flow in a detectable way, for example by means of a flow meter. The obstruction does not have to be a full closure of the mouth; it is sufficient that the difference between free flow and obstructed flow is detectable (for example 5× smaller).

Such a high liquid level detection means 202-205 provides a simple construction for detecting when the liquid level in the vessel becomes too high. Firstly, the fact that there is no need for a complete closing off of the mouth of the inlet tube means that no perfect seal is needed. In the context of the gastrointestinal tract simulation system, it is not necessary to perform a continuous measurement, so the gas flow to detect the liquid level may be intermittent; it may in fact only be required at short time intervals. The gas flow may be as small as 1 Nl/min with floater down and 0.1 Nl/min with floater up, so the pressure in the head space above the liquid is stays substantially stable. The size/footprint of these detection means on the lid ceiling may be as small as 5×5 mm. The holder 205 construction can be fully integrated in the 3D printed holding element described elsewhere herein. For the gas supply and flow meter, devices which are already present in the system can be used.

In embodiments, the compartments of the gastrointestinal tract simulation system described herein may comprise tubing for transferring the following fluids: nutritional medium, gastric secretion solution, pancreatic juice, bile, small intestinal media and colon suspension. Furthermore, the compartments may be equipped with the following sensors: pH probes, redox probes, temperature sensors, level sensors, dissolved oxygen sensors, pressure sensors.

An embodiment of the invention provides method of simulating the functioning of the human or animal gastrointestinal tract, comprising the steps of filling empty compartments of a gastrointestinal tract simulation system as described herein with fluids simulating the physiological fluids of the gastrointestinal tract and operating the gastrointestinal tract simulation system so as to control, in each of the compartments, one or more or all of the following parameters: liquid flow (e.g. 0-10 ml/min), temperature (e.g. 20-50° C.), pH (e.g. ranging from 1 to 9), ionic strength (e.g. ranging from 0 to 10 M), head space (e.g. between 0 and 100 ml), stirring (e.g. 0-600 rpm), pressure (e.g. 0-2 bar), liquid volume (e.g. 0-100 ml), each in accordance with pre-determined values, ranges or trajectories. Preferred ranges are: liquid flow 0.1-6 ml/min, temperature 35-40° C., pH ranging from 1.5 to 8, ionic strength ranging from 0.01 to 5M, head space between 1 and 50 ml, stirring 1-500 rpm, pressure 0.1-1.5 bar, liquid volume 5-50 ml.

In embodiments, the method comprises a first step of sterilizing the interior of the gastrointestinal tract simulation system by introducing $H_2O_2$ gas into the empty compartments and/or by increasing the interior temperature of the compartments to a value within the range of 40° C. to 121° C. (15 psi) for a period of time within the range of 30 minutes.

In embodiments, the gastrointestinal tract simulation system is operated to transfer, at pre-determined rates, nutritional medium from a first reservoir to a first compartment (5-50 ml); simulated gastric fluid from a second reservoir to a first compartment (0-10 ml); pancreatic fluid from a third reservoir to a third compartment (0-20 ml); and the content of each compartment to a consecutive compartment according to the requested retention time.

In embodiments, the method comprises the step of introducing a test sample in a compartment of the gastrointestinal tract simulation system, wherein said test sample is selected from the group consisting of micro-organism samples, pharmacologically active agents, pharmaceutical formulations, minerals, food and feed compounds and dietary fibers.

In embodiments, a plurality of said gastrointestinal tract simulation systems are operated simultaneously and identically, and wherein one or more of said gastrointestinal tract simulation systems contain a test sample and one or more of the gastrointestinal tract simulation systems do not contain a test sample.

Figure 10:
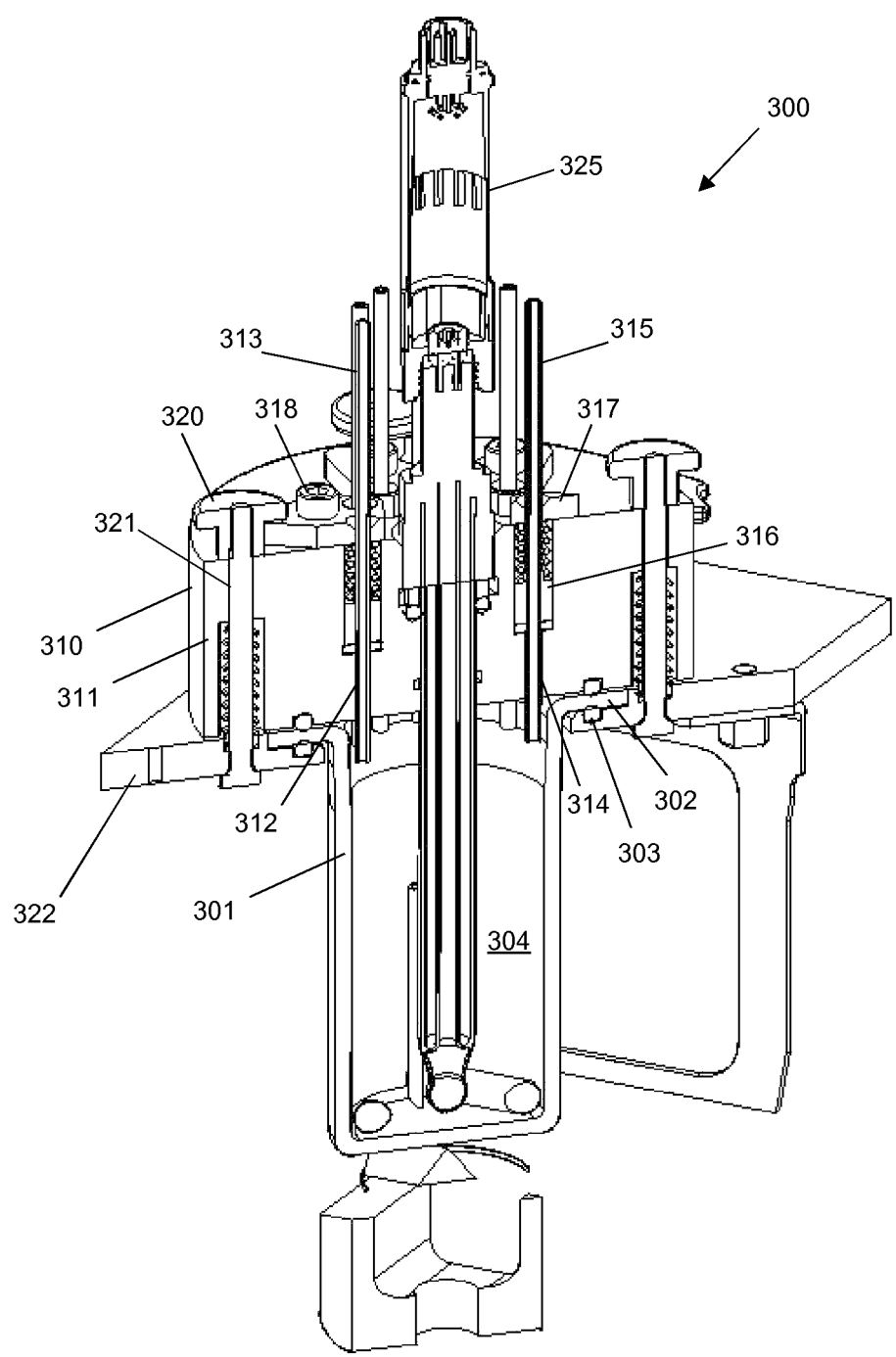
FIGS. 10-12 show views of another embodiment of a compartment for a gastrointestinal tract simulating system according to an embodiment of the invention.
Figure 11:
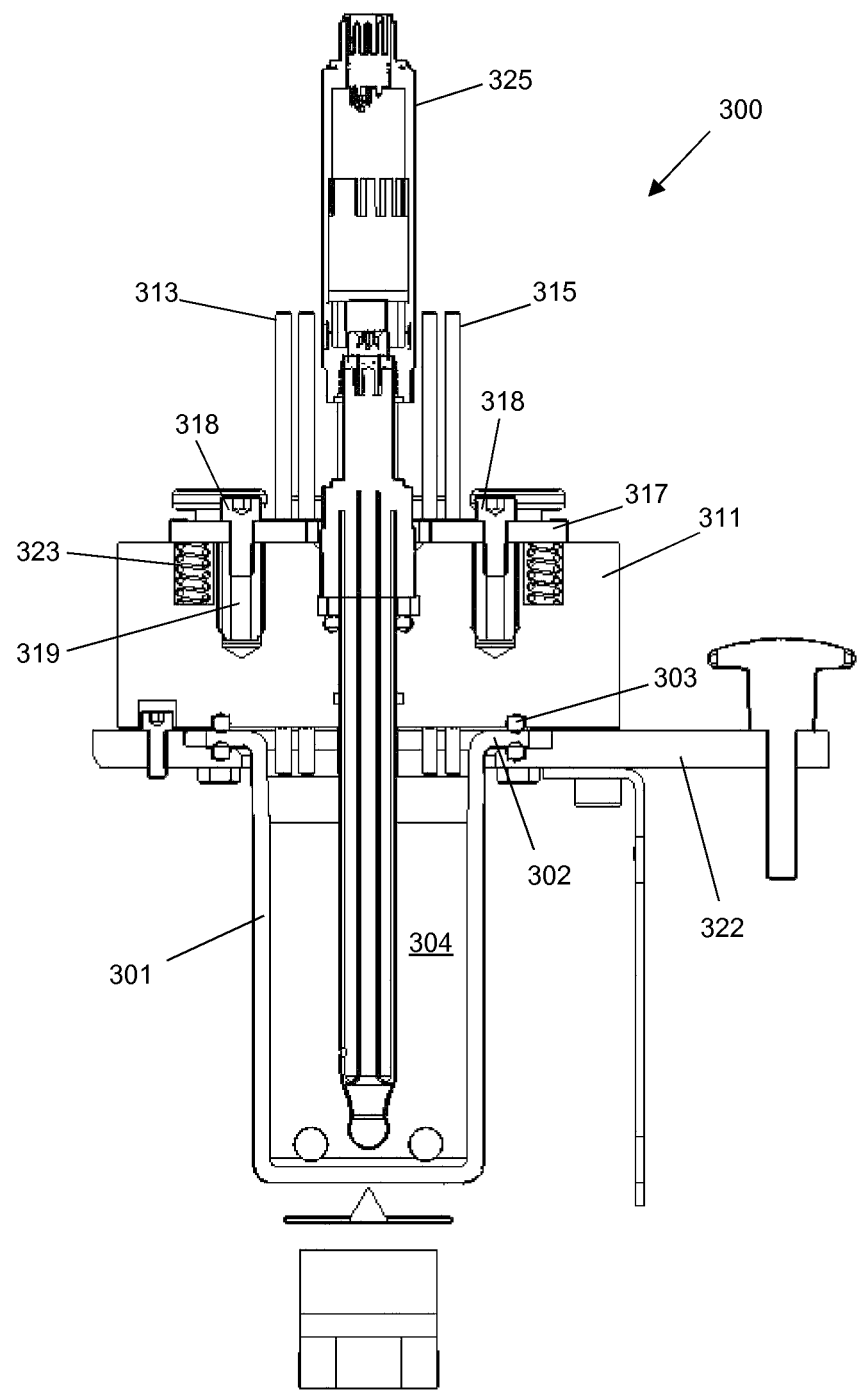
Figure 12:
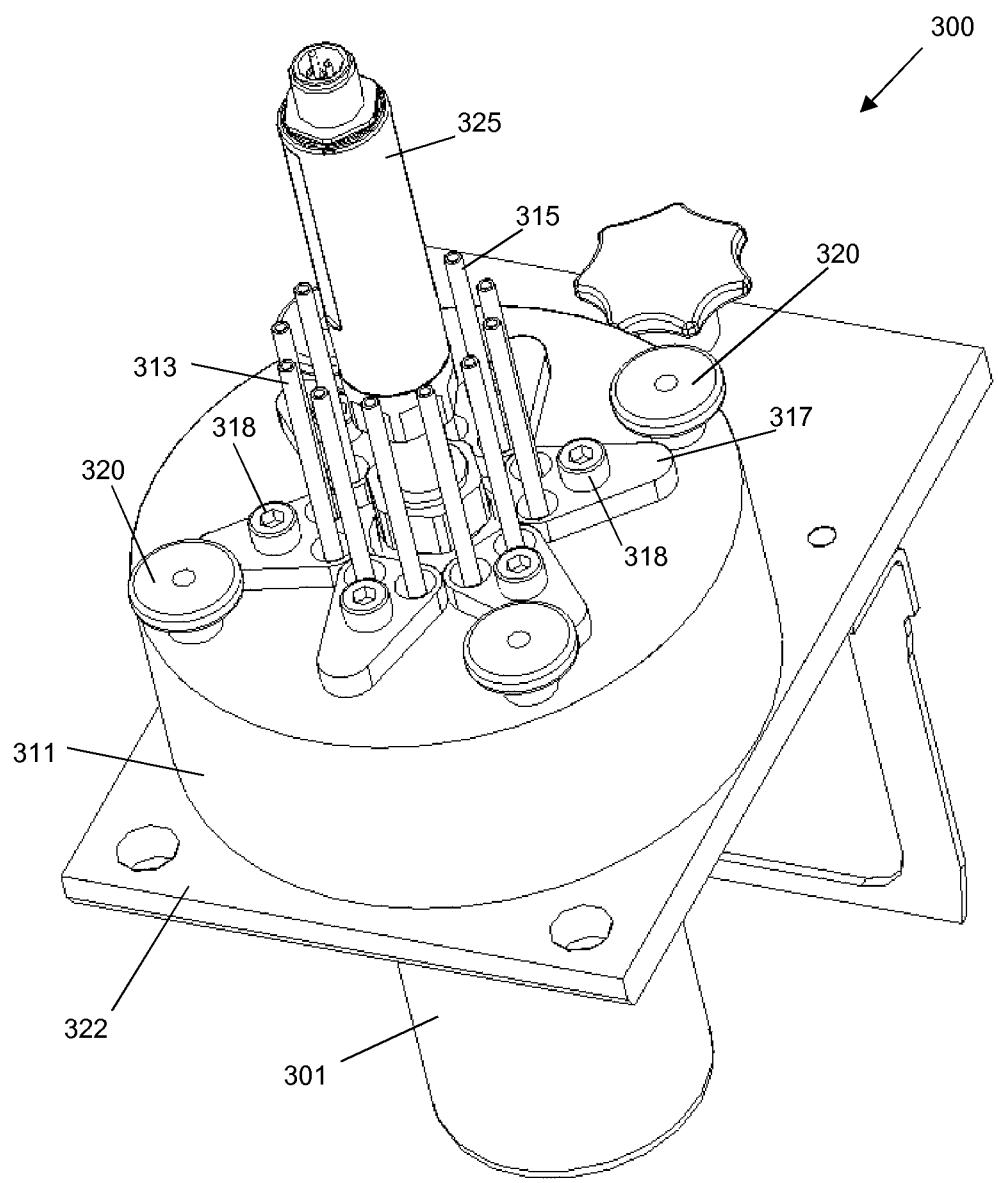

FIGS. 10-12 show cross-sectional and perspective views of another embodiment of a gastrointestinal tract simulating system according to the invention, comprising a compartment 300 (also called reactor) having a vessel 301 having an open top surrounded by a peripheral edge portion or flange 302 and an air-tight lid system 310 configured to be placed onto the peripheral edge portion and to form an air-tight seal between the lid system and the vessel. This means that the lid system 310 is configured to fit on the peripheral edge portion 302 in such a way that, following a step of fixing the lid system on said edge portion, an air-tight seal is obtained. This can be achieved in many ways, for example involving one or more sealing rings 303, which are known per se to the person skilled in the art, and therefore need not be further described herein.

The lid system comprises a body 311 with a plurality of passageways 312, 314 extending through the body and providing access to the interior 304 of the vessel, the plurality of passageways comprising first passageways 312 configured for receiving fluid transfer tubes 313 and second passageways 314 configured for mounting at least one sensor component 315 (which may also comprise tubing), extending vertically through the lid system. The first and/or second passageways 312, 314 are sized and formed for receiving fluid transfer tubes (for transferring liquids and/or gases), resp. a sensor component or sensor tubing, in such a way that they preferably fit tightly around the tubes and guide them between the point of entry into the lid system (top side) and the point of exit (bottom side) towards the interior of the vessel.

The lid system 310 is preferably provided with releasable sealing elements 316 for sealing at least the first passageways and one or more pressing elements 317 which are common to at least a number of the sealing elements and configured for applying pressure to each of the sealing elements to effect the sealing of the plurality of passageways. The principle is the same as shown in FIG. 2, the sealing elements 316 each comprise a helical spring, a cylindrical member and a resilient sealing ring, which in use surround the tubing with the sealing ring being compressed onto and around the tubing. By this construction, the air-tight sealing of the compartment may be facilitated and/or simplified. One only needs to operate the pressing element 317 to effect, or release, the sealing of all of the number of passageways by the sealing elements 316, or at least those passageways which have a sealing element operated by the common pressing element 317. A further advantage of this structure is that it makes it possible to miniaturize the compartments of the gastrointestinal tract simulation system.

In embodiments, the releasable sealing elements 316 may each comprise a sealing member in a sealing material, provided for being compressed onto or around the respective tube or sensor component which is inserted in the respective passageway, and a spring member, for example a helical spring, acting on the sealing member to effectuate said compression. This provides a simple construction for the sealing elements.

In embodiments, the pressing element may comprise a plate-like member 317 which is movably fixed to the body of the lid system between a pressing position, in which the plate-like member applies the pressure to the sealing elements to effect the sealing of the passageways, and a release position, in which the sealing elements are in released state. The movable fixture may for example be carried out by means of one or more screws 318, wherein the plate-like member is movable from the release position to the pressing position by screwing in the one or more screws, and vice versa. This embodiment may provide a simple construction for the pressing member.

As shown in the embodiment of FIGS. 10-12, the passageways 312, 314, the holes or bores 319 for receiving fixing screws 318 for fixing the plate-like member 317, holes or bores 321 for receiving fixing screws or bolts 320 for fixing and sealing the lid system onto the vessel (using plate 322 which accommodates the flange of the vessel), and also other holes or bores, may extend vertically through the lid system. This facilitates manufacturing of the body 311 of the lid system, as all these holes can be made into the body in the same direction, e.g. by drilling. The body 311 of the lid system may be a cylindrical body as shown, for example manufactured in a plastic material. The vessel 301 is preferably manufactured in a transparent material to enable visual inspection of the contents of the compartment.

The compartment 300 may be equipped with a pH probe 325, as shown, which may be centrally located and provided through the body 311. The passageways 314, 315 may be radially spaced around the central opening for the pH probe, so as to minimize the space occupied by the passageways and reduce the size of the lid system.

As shown, the plate-like member 317 may be star-shaped, with each point being fixed to the body by means of a screw 318 which is held in bore 319, and each point compressing a spring 323. The star shape is advantageous as it leaves space for operating the bolts 320 by means of which the body 311 is fixed to the plate 322 and the flange 302 of the vessel 301 is sealed in between them. Alternatively, the plate-like member may have any shape with cut-outs providing space for these fixing screws or other fixing means 320, e.g. triangular, plus-shaped, circular with cut-outs, etc.

As shown, the plate-like member 317 and also the body 311 are rotationally symmetric parts, which may contribute to reducing manufacturing complexity and/or miniaturization of the lid system.

In embodiments, as a result of the structure described above, the compartments of the gastrointestinal tract simulation system may be miniaturized such that the vessel has, for example, an inner volume ranging from 5 ml to 100 ml.

The invention claimed is:

1. A compartment of a gastrointestinal tract simulation system, comprising
  a vessel having an open top surrounded by a peripheral edge portion and an air-tight lid system configured to be placed onto the peripheral edge portion and to form an air-tight seal between the lid system and the vessel,
  wherein the lid system comprises a body with a plurality of passageways extending through the body and providing access to the interior of the vessel, said plurality of passageways comprising first passageways configured for receiving fluid transfer tubes and second passageways configured for mounting at least one sensor component,
  wherein the lid system is provided with releasable sealing elements for sealing the plurality of passageways and at least one pressing element which is common to at least a number of the sealing elements and configured for applying pressure to each of the respective sealing elements to effect the sealing of the respective passageways, and
  wherein the pressing element comprises a plate-like member which is movably fixed to the body of the lid system between a pressing position, in which the plate-like member applies the pressure to the sealing elements to effect the sealing of the passageways, and a release position, in which the sealing elements are in released state.

2. The compartment according to claim 1, wherein the releasable sealing elements each comprise a sealing member, provided for being compressed onto or around a respective tube or sensor component which is inserted in the respective passageway, and a spring member acting on the sealing member for said compression.

3. The compartment according to claim 1, wherein the plate-like member is movable from the release position to the pressing position by screwing in one or more screws.

4. The compartment according to claim 1, wherein the plate-like member comprises cut-outs leaving space for fixing screws, by means of which the body of the lid system and the vessel are sealed to each other.

5. The compartment according to claim 1, comprising a sensor probe extending vertically through the lid system into the vessel.

6. The compartment according to claim 1, wherein the passageways extend vertically through the lid system.

7. The compartment according to claim 1, comprising a sensor probe extending vertically through the lid system into the vessel, wherein the passageways extend vertically through the lid system and are radially spaced around the sensor probe.

8. The compartment according to claim 1, wherein the body and the pressing element are rotationally symmetric parts.

9. A gastrointestinal tract simulation system comprising at least one compartment, each compartment comprising
  a vessel having an open top surrounded by a peripheral edge portion and an air-tight lid system configured to be placed onto the peripheral edge portion and to form an air-tight seal between the lid system and the vessel,
    wherein the lid system comprises a body with a plurality of passageways extending through the body and providing access to the interior of the vessel, said plurality of passageways comprising first passageways configured for receiving fluid transfer tubes and second passageways configured for mounting at least one sensor component,
    wherein the lid system is provided with releasable sealing elements for sealing the plurality of passageways and at least one pressing element which is common to at least a number of the sealing elements and configured for applying pressure to each of the respective sealing elements to effect the sealing of the respective passageways, and wherein the pressing element comprises a plate-like member which is movably fixed to the body of the lid system between a pressing position, in which the plate-like member applies the pressure to the sealing elements to effect the sealing of the passageways, and a release position, in which the sealing elements are in released state;

fluid transfer tubes extending through the respective first passageways, and sensor components mounted in or on the second passageways.

10. The gastrointestinal tract simulation system according to claim 9, wherein the gastrointestinal tract simulation system further comprises a water bath in which at least one vessel of the at least one compartment is placed and at least one magnetic stirring system for stirring the contents of at least one vessel, each magnetic stirring system comprising a magnetic drive mounted underneath the respective vessel and the water bath and provided for generating a rotating magnetic field, a permanent magnet located in the water bath underneath the respective vessel and provided for rotating with and amplifying said rotating magnetic field, and a first stirring element at the bottom of the respective vessel provided for being rotated by said amplified magnetic field.

11. The gastrointestinal tract simulation system according to claim 10, wherein the vessel of the respective compartment is an outer vessel and the compartment further comprises an inner vessel mounted inside the outer vessel and a second stirring element at the bottom of the inner vessel, provided for being rotated by the amplified magnetic field.

12. The gastrointestinal tract simulation system according to claim 11, wherein the second stirring element is a permanent magnet.

13. The gastrointestinal tract simulation system according to claim 10, wherein the first stirring element is a permanent magnet.

14. The gastrointestinal tract simulation system according to claim 10, wherein at least one of the permanent magnets and/or stirring elements is generally triangular prism-shaped.

15. The gastrointestinal tract simulation system according to claim 9, wherein at least one compartment has an outer vessel and an inner vessel mounted inside the outer vessel, the inner vessel having a wall at least part of which is formed by a dialysis membrane.

16. The gastrointestinal tract simulation system according to claim 15, wherein the inner vessel wall comprises a cylindrical grid structure, the dialysis membrane being mounted around said cylindrical grid structure.

17. The gastrointestinal tract simulation system according to claim 9, wherein at least one compartment contains carriers covered with mucin representative of the mucus layer lining the gut wall to simulate a mucosal compartment that can support the colonization of microbial species which may grow attached to the gut wall in humans and animals.

18. The gastrointestinal tract simulation system according to claim 9, wherein the lid system of the at least one compartment is provided with a high liquid level detection means for detecting a too high liquid level in the vessel, the high liquid level detection means comprising a gas inlet tube and a gas outlet tube through the lid system and a means for establishing a gas flow through said gas inlet and outlet tubes and via a head space in said vessel, wherein a floater is mounted at a mouth of at least one of the gas inlet and outlet tubes, said floater being adapted for being raised, by floating on the liquid in the vessel if the level of said liquid becomes too high, from a free flow position in which the floater forms no obstruction for said gas flow to an obstructing position in which the floater forms an obstruction for said gas flow.

19. A method of simulating the functioning of the human or animal gastrointestinal tract, comprising the steps of filling empty compartments of a gastrointestinal tract simulation system as provided in claim 12 with fluids simulating the physiological fluids of the gastrointestinal tract and operating the gastrointestinal tract simulation system so as to control, in each of the compartments, one or more or all of the following parameters: liquid flow, temperature, pH, ionic strength, head space, stirring, pressure, liquid volume, each in accordance with predetermined values, ranges or trajectories.

* * * * *